United States Patent
Deweese et al.

(10) Patent No.: US 6,600,997 B2
(45) Date of Patent: Jul. 29, 2003

(54) ANALYTE TEST INSTRUMENT HAVING IMPROVED CALIBRATION AND COMMUNICATION PROCESSES

(75) Inventors: Marshall D. Deweese, Newton, MA (US); Leonidas Carayannopoulos, Somerville, MA (US); Joel M. Parks, Bedford, MA (US); William H. Ames, Holden, MA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/017,447

(22) Filed: Dec. 14, 2001

(65) Prior Publication Data

US 2002/0082797 A1 Jun. 27, 2002

Related U.S. Application Data

(62) Division of application No. 09/441,563, filed on Nov. 17, 1999, now Pat. No. 6,377,894.
(60) Provisional application No. 60/110,227, filed on Nov. 30, 1998.

(51) Int. Cl.[7] .............................................. G06F 19/00
(52) U.S. Cl. ....................................................... 702/22
(58) Field of Search ........................... 702/22, 25, 184; 128/419, 421, 200.14; 235/462; 436/518; 435/5, 6; 204/403.04, 403.03, 403.01; 422/68.1

(56) References Cited

U.S. PATENT DOCUMENTS

| | | | |
|---|---|---|---|
| 4,065,263 A | | 12/1977 | Woodbridge, III |
| 4,297,569 A | | 10/1981 | Flies |
| 4,329,642 A | | 5/1982 | Luthi et al. |
| 4,545,382 A | | 10/1985 | Higgins et al. |
| 4,552,458 A | | 11/1985 | Lowne |
| 4,600,010 A | * | 7/1986 | Dugot ......................... 607/27 |

(List continued on next page.)

FOREIGN PATENT DOCUMENTS

| | | |
|---|---|---|
| DE | 297 02 277 | 4/1997 |
| EP | 0 651 250 | 5/1995 |
| GB | 2 322 207 | 8/1998 |
| WO | 97/08544 | 3/1997 |
| WO | 97/29847 | 8/1997 |
| WO | 98/19159 | 5/1998 |

*Primary Examiner*—Kamini Shah
(74) *Attorney, Agent, or Firm*—David L. Weinstein

(57) ABSTRACT

An analyte test instrument having improved calibration and communication processes. The instrument employs a calibration method that allows it to communicate with any one of a plurality of data storage strips. A data storage strip including a memory device is inserted into the test port of the instrument. The data storage strip is identified, and the instrument establishes communications with the data storage strip using a protocol corresponding to the data storage strip. Second, the instrument employs a method for ensuring that the instrument is operated using valid calibration strips and test strips. The instrument determines whether one or more of test parameters stored in the instrument is invalid for a test strip inserted into the test port of the instrument. If a test parameter is invalid, an indication of the invalid strip parameter is displayed on the display. Finally, the instrument utilizes a method for determining the actual date and time of events that occurred before the instrument was provided with current date and time.

7 Claims, 9 Drawing Sheets

U.S. PATENT DOCUMENTS

| | | | |
|---|---|---|---|
| 4,612,620 A | * 9/1986 | Davis et al. ................. 702/184 |
| 4,628,193 A | 12/1986 | Blum |
| 4,648,665 A | 3/1987 | Davis et al. |
| 4,711,245 A | 12/1987 | Higgins et al. |
| 4,714,874 A | 12/1987 | Morris et al. |
| 4,806,311 A | 2/1989 | Greenquist |
| 4,806,312 A | 2/1989 | Greenquist |
| 4,810,203 A | 3/1989 | Komatsu |
| 4,820,636 A | 4/1989 | Hill et al. |
| 4,857,716 A | * 8/1989 | Gombrich et al. ........... 128/903 |
| 4,954,087 A | 9/1990 | Lauks et al. .................... 439/7 |
| 5,039,618 A | 8/1991 | Stone ........................... 436/77 |
| 5,053,199 A | 10/1991 | Keiser et al. .............. 422/68.1 |
| 5,096,669 A | 3/1992 | Lauks et al. ........... 204/403.02 |
| 5,141,850 A | 8/1992 | Cole et al. .................. 436/525 |
| 5,182,707 A | 1/1993 | Cooper et al. ................. 422/55 |
| 5,234,813 A | 8/1993 | McGeehan et al. ........... 435/7.9 |
| 5,363,842 A | * 11/1994 | Mishelevich et al. .. 128/200.14 |
| 5,366,609 A | 11/1994 | White et al. ........... 204/403.04 |
| 5,376,254 A | 12/1994 | Fisher ................... 204/403.01 |
| 5,395,504 A | 3/1995 | Saurer et al. .......... 204/403.03 |
| 5,447,837 A | 9/1995 | Urnovitz ........................ 435/5 |
| 5,477,326 A | 12/1995 | Dosmann .................... 356/406 |
| 5,500,350 A | 3/1996 | Baker et al. ................ 435/7.92 |
| 5,508,200 A | 4/1996 | Tiffany et al. ................. 436/44 |
| 5,509,410 A | 4/1996 | Hill et al. .................... 600/393 |
| 5,532,128 A | 7/1996 | Eggers et al. .................. 435/6 |
| 5,556,789 A | 9/1996 | Goerlach-Graw et al. .. 436/169 |
| 5,569,608 A | 10/1996 | Sommer ..................... 436/518 |
| 5,604,110 A | 2/1997 | Baker et al. ................ 435/7.92 |
| 5,605,662 A | 2/1997 | Heller et al. .............. 422/68.1 |
| 5,628,890 A | 5/1997 | Carter et al. ........... 204/403.05 |
| 5,639,671 A | 6/1997 | Bogart et al. ............... 436/518 |
| 5,645,798 A | 7/1997 | Schreiber et al. .............. 422/58 |
| 5,654,178 A | 8/1997 | Fitzpatrick et al. ...... 435/70.21 |
| 5,658,802 A | 8/1997 | Hayes et al. ................ 436/518 |
| 5,682,884 A | 11/1997 | Hill et al. .............. 204/403.04 |
| 5,695,623 A | 12/1997 | Michel et al. .......... 204/403.05 |
| 5,873,990 A | 2/1999 | Wojciechowski et al. ... 204/406 |
| 5,989,917 A | 11/1999 | McAleer et al. .............. 436/46 |

\* cited by examiner

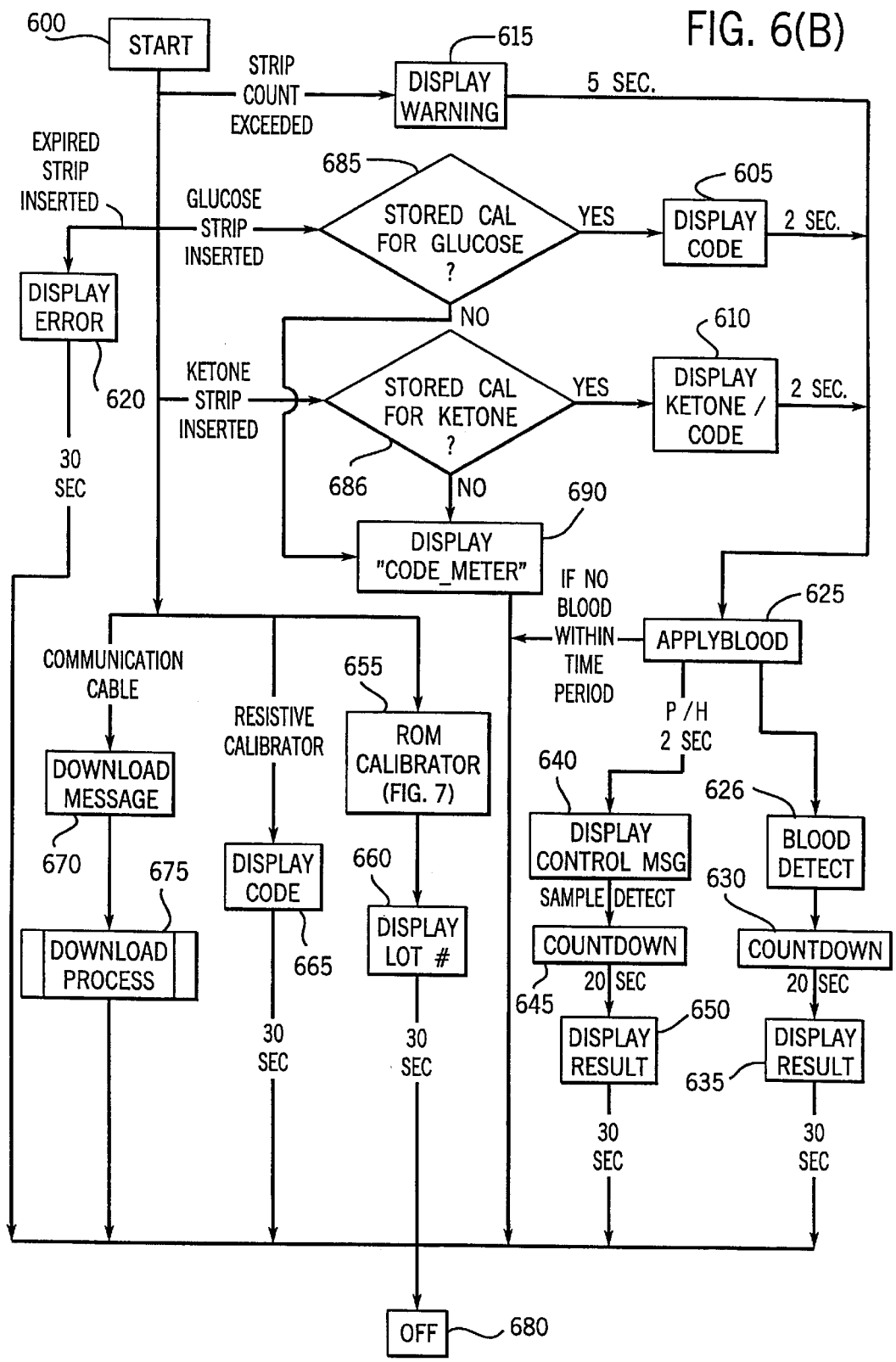

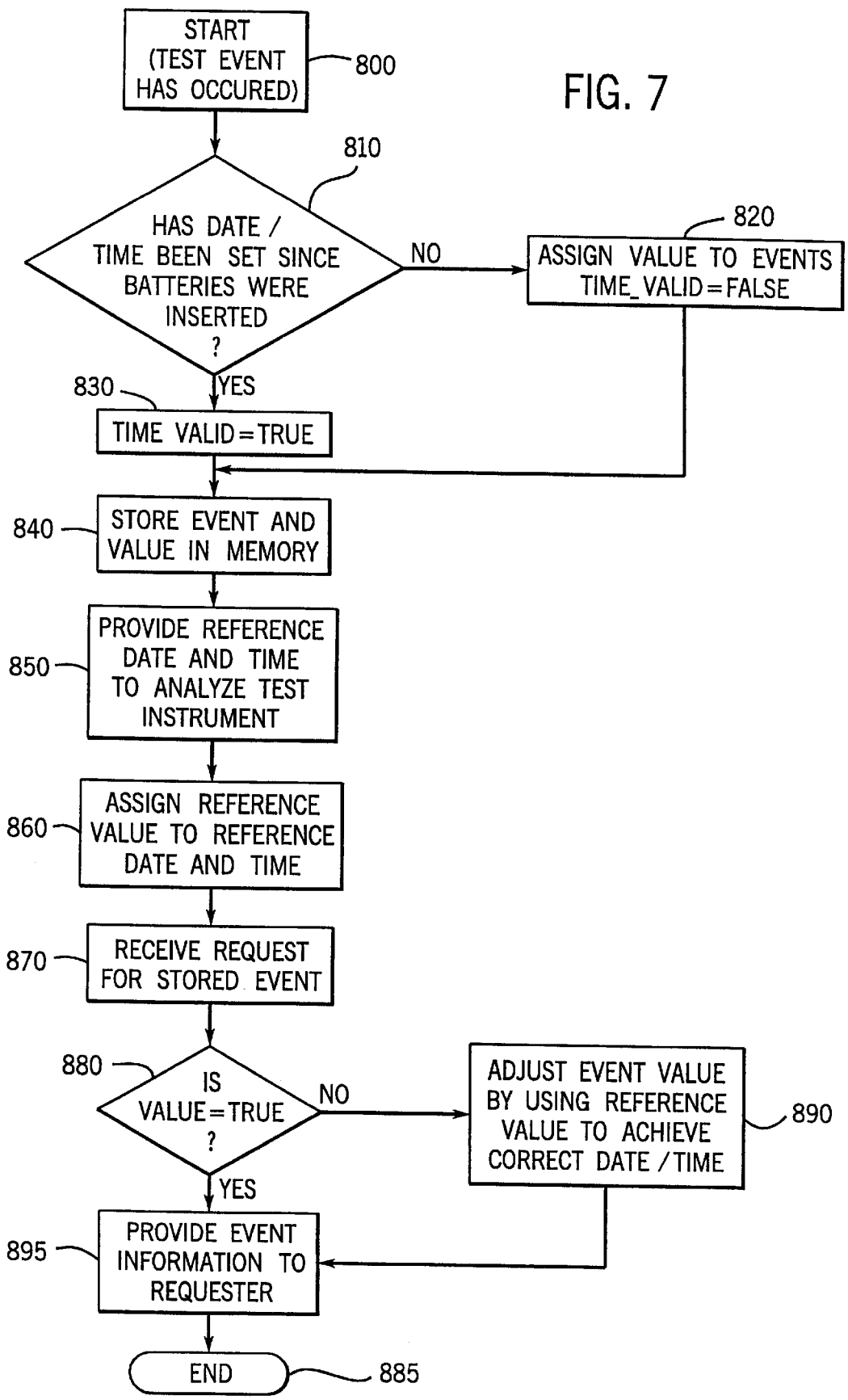

ANALYTE TEST INSTRUMENT HAVING IMPROVED CALIBRATION AND COMMUNICATION PROCESSES

This application is a divisional of U.S. Ser. No. 09/441,563, U.S. Pat. No. 6,377,894 filed Nov. 17, 1999, which claims priority from the provisional application Ser. No. 60/110,227, filed Nov. 30, 1998.

CROSS-REFERENCE TO RELATED APPLICATIONS

This application is a co-pending application of an application Ser. No. 09/441,674 filed on evendate herewith, and entitled, "Multichemistry Measuring Device and Test Strips" (hereinafter "Multichemistry Application"), the contents of which are incorporated herein by reference.

BACKGROUND OF THE INVENTION

1. Field of the Invention

This invention relates to analyte test instruments that perform electrochemical assays on biological samples. More particularly, the invention relates to analyte test instruments having improved calibration and communication processes.

2. Discussion of the Art

An analyte test instrument can be used to perform electrochemical assays (e.g., glucose concentration) on biological samples (e.g., blood). To operate such an instrument, a user inserts a test strip into a test port in the instrument. The instrument displays a "ready" indication to the user and waits for the user to deposit a biological sample on the test strip. When a sufficient quantity of material is deposited on the reaction area of the test strip, an electrochemical reaction occurs. The electrochemical reaction causes a flow of electrons, which produces an electrical signal, such as a change in current, detectable by the instrument. The instrument converts the detected signal into data that corresponds to analyte information and displays the information to the user. The instrument may have the capability to store a plurality of such measurements and provide this information to the user via a display or to an external processor via a data link.

Analyte test instruments for electrochemical assays often require the user to use periodically calibrate the instrument. One known calibration technique is described in U.S. Pat. No. 5,366,609 to White et al. The disclosed instrument requires a removably insertible read-only-memory (ROM) key for operation and calibration of the instrument. The ROM key is inserted into a port, which is distinct from the test port, and must remain in the instrument during operation and calibration testing. A test strip is inserted into the test port after the ROM key is inserted into the ROM key port. The ROM key contains batch-specific constants and data required for carrying out analyte determination procedures on biological material applied to the test strips. In addition, the ROM key can contain some or all of the code that controls the testing. A microprocessor in the instrument uses the constants, conversion factors, and code provided by the ROM key on an "as-needed basis" to perform tests.

Another calibration technique is employed by the PRECISION Q.I.D blood glucose testing system manufactured and sold by MEDISENSE, Inc., Bedford Mass. The instrument has a single port that separately receives both calibration strips and test strips. A calibration strip including data and constants specific to a given batch of test strips, including the batch code for the test strips, is provided with each batch of test strips. Typically, when a new box of test strips is opened, the user first inserts the calibration strip into the test port to calibrate the instrument. The user then removes the calibration strip, and the instrument is ready to receive test strips. The instrument stores the batch code for the calibration strip and displays that code to the user. Thus, the user can manually verify that the batch code matches the code printed on each test strip being used. The calibration data for the instrument is specific to those test strips having the same batch code and remains stored in the instrument until another calibration strip is inserted.

Although manufacturers of analyte test instruments take great care in providing accurate calibration devices and detailed instructions on the calibration process, errors attributable to the calibration process frequently contribute to erroneous test readings. For example, known instruments do not alert the user to prevent running a test with a test strip that is not matched to the calibration of the instrument or with a test strip that has expired. In addition, known instruments do not have the capability of performing a multiplicity of different assays with a single measuring apparatus having a broad spectrum of testing functionalities without having to manually reconfigure the instrument.

SUMMARY OF THE INVENTION

The present invention provides an analyte test instrument having improved calibration and communication processes. These improved processes allow greater ease in calibration, greater ease in operation, and greater versatility. The processes also provide more reliable results than do presently available instruments.

In one aspect, the invention features a calibration method for an analyte test instrument that uses one of a plurality of data storage strips. The data storage strips can include one or more memory devices, such as a ROM device, that stores calibration and test data. The analyte test instrument includes a test port adapted to receive any one of a plurality of data storage strips, a processor electrically connected to the test port, and a memory storing a protocol for communicating with each data storage strip. The instrument receives a data storage strip in the test port. The instrument polls the test port to identify the data storage strip. When the data storage strip has been identified, the instrument establishes communications with the data storage strip using the protocol that corresponds to the data storage strip.

In one embodiment, data from the data storage strip is downloaded by the instrument and stored in the memory. The data can comprise instrument parameters (e.g., language and instrument type), test strip parameters (test strip count and expiration date), and analyte parameters. The data storage strip is removed from the test port, and a test strip can be inserted in the test port. Using the downloaded data, the instrument implements a test procedure to perform an analyte test when biological material is supplied, such as when a user provides a sample.

In another aspect, the invention provides a method for ensuring that an analyte test instrument is operated using valid calibration and test strips. The instrument includes a test port adapted to receive a calibration strip or a test strip, a processor electrically connected to the test port, a memory storing a plurality of test parameters, and a display for displaying information to a user. The instrument receives into the test port a calibration strip or a test strip. The processor accesses the test parameters stored in the memory to determine whether one or more of the test parameters is invalid for the test strip. If a test parameter is invalid, an indication of the invalid test strip parameter is displayed on the display.

In one embodiment, the test parameters can include test strip count and expiration date, instrument language, and instrument type. In some embodiments, the processor disables the instrument when certain parameters are invalid. In other embodiments, a warning is displayed when certain parameters are invalid.

In yet another aspect, the invention features a method for determining the actual date and time of events in a battery-operated analyte test instrument. Events generated by operation of the battery-operated analyte test instrument are stored in the memory. A value is assigned to each event when such event is stored in the memory. At some point, a reference date and time are provided to the battery-operated analyte test instrument (e.g., these are entered via the user interface). A reference value is assigned to the reference date and time. The actual date and time of each event are computed by adjusting the value assigned to each event using the reference value.

In still another aspect, the invention provides a method for controlling the operation of an analyte test instrument. A data storage strip is received into the test port and is polled to identify its type. Communications are established with the data storage strip, using the protocol corresponding to the data storage strip, when the data storage strip is identified. Data is then downloaded from the data storage strip into the analyte test instrument, and the analyte test instrument stores the data even after the data storage strip is removed. In some embodiments, the downloaded data comprises at least a portion of a test procedure that the analyte test instrument uses to perform diagnostic tests. In another embodiment, the analyte test instrument has stored on it a plurality of test procedures used to conduct one or more diagnostic tests using the analyte test instrument. In this embodiment, a control procedure that selects one or more of the stored procedures to run is downloaded. In this manner, the data storage strip can reconfigure the analyte test instrument "in the field" to run different types of tests or combinations of tests.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. These and other features of the invention are more fully described below in the detailed description and accompanying drawings, in which:

FIG. 6B is a flow chart illustrating strip insertion flow in accordance with one embodiment of the invention.

FIG. 7 is a flow chart illustrating date and time determination in accordance with one embodiment of the invention.

DETAILED DESCRIPTION

The present invention features an analyte test instrument having improved calibration and communication processes, allowing the instrument to be more versatile and easier to calibrate and operate. Before describing the detailed features and embodiments of the invention, the following definitions are provided to assist in an understanding of the terminology used.

"Sample" describes both an activity and an interim measurement resulting from that activity, occurring when a sample of blood or fluid is applied to a test strip and is then excited with a pulse voltage. An analog signal is detected, then the analog signal is converted to a digital result that is used as a sample. A "glucose assay" is an analysis that determines the amount of glucose present in a sample. A "ketone assay" is an analysis that determines the amount of ketones present in a sample. "Phase" describes the time intervals into which an assay is divided.

Figure 1A:
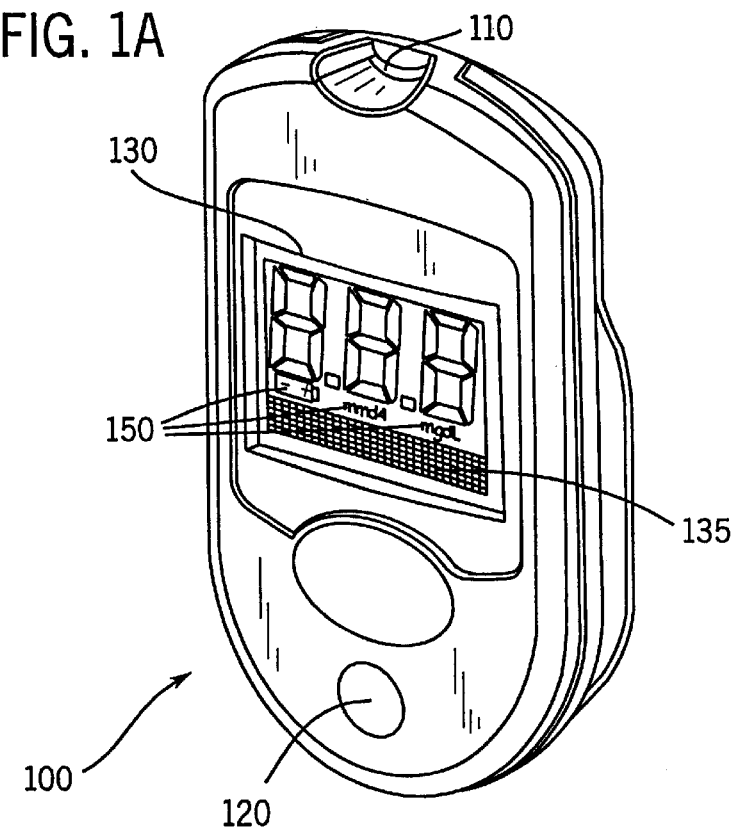
FIG. 1A is a front perspective view of an analyte test instrument in accordance with an embodiment of the invention.
Figure 2:
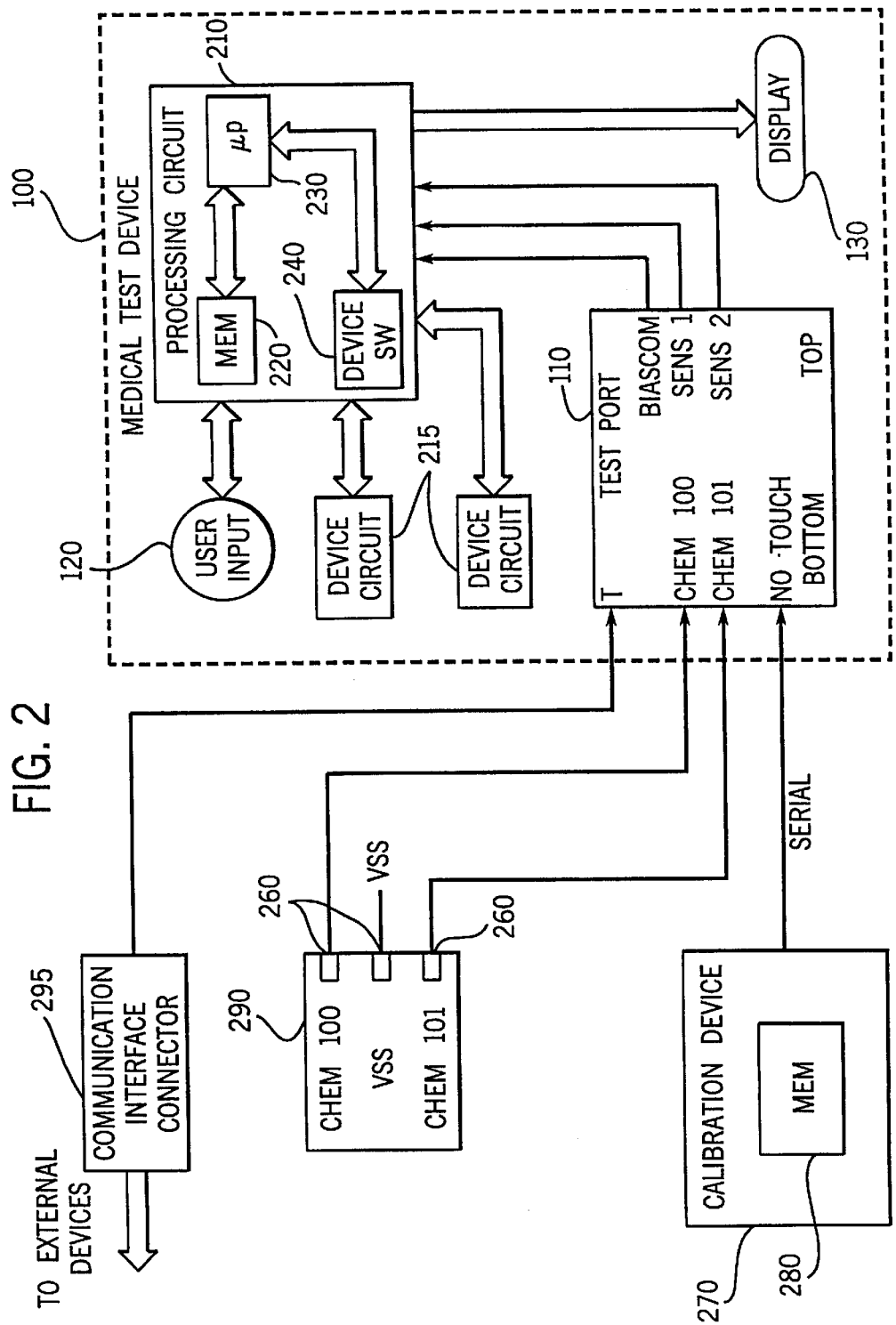
FIG. 2 is a block diagram of an analyte test instrument system in accordance with the present invention.

FIG. 1A is an illustration of an instrument 100 that operates in accordance with one embodiment of the invention. The exterior of the instrument 100 comprises a display 130, a push-button 120, and a test port 110. A push-button 120 provides user control of the analyte test instrument 100. In particular, the push-button 120 is used to turn the instrument on and off, recall information stored in the instrument, respond to displayed messages, and set some of the configuration control parameters for the instrument. The push-button 120 can also provide access to menus generated by device software 240 (FIG. 2).

In one embodiment, one or more replaceable batteries (not shown) installed via the rear side of the instrument provide power for the analyte test instrument 100. It should be understood, however, that any source of power capable of providing a suitable direct current (DC) voltage can provide power to the instrument 100.

Figure 3A:
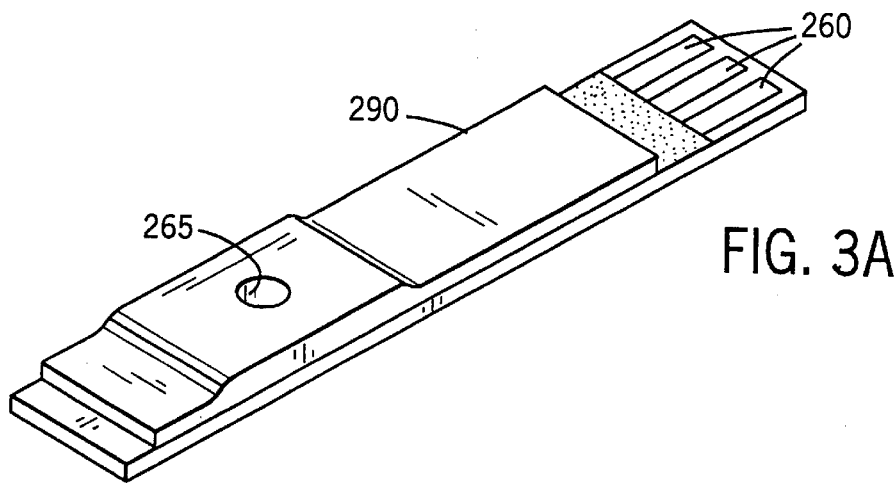
FIG. 3A is a perspective cut-away view of a test strip in accordance with one embodiment of the invention.
Figure 3B:
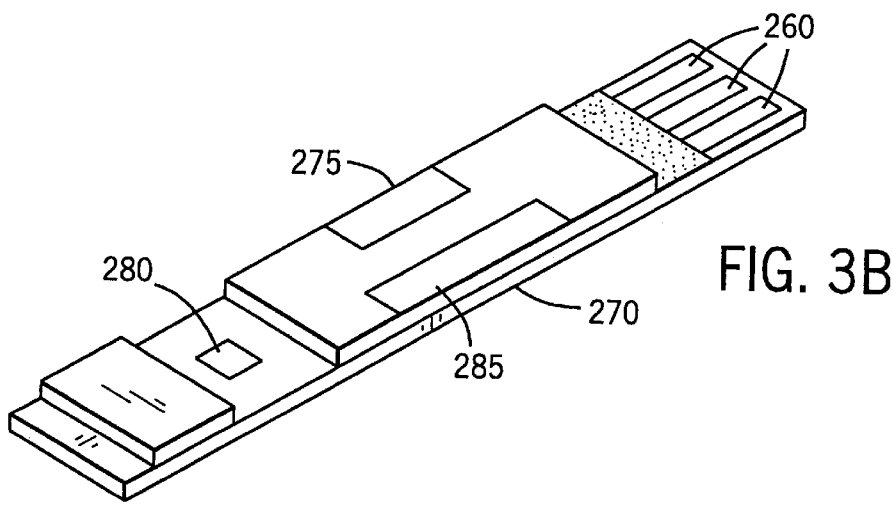
FIG. 3B is a perspective cut-away view of a calibration strip in accordance with one embodiment of the invention.
Figure 3C:
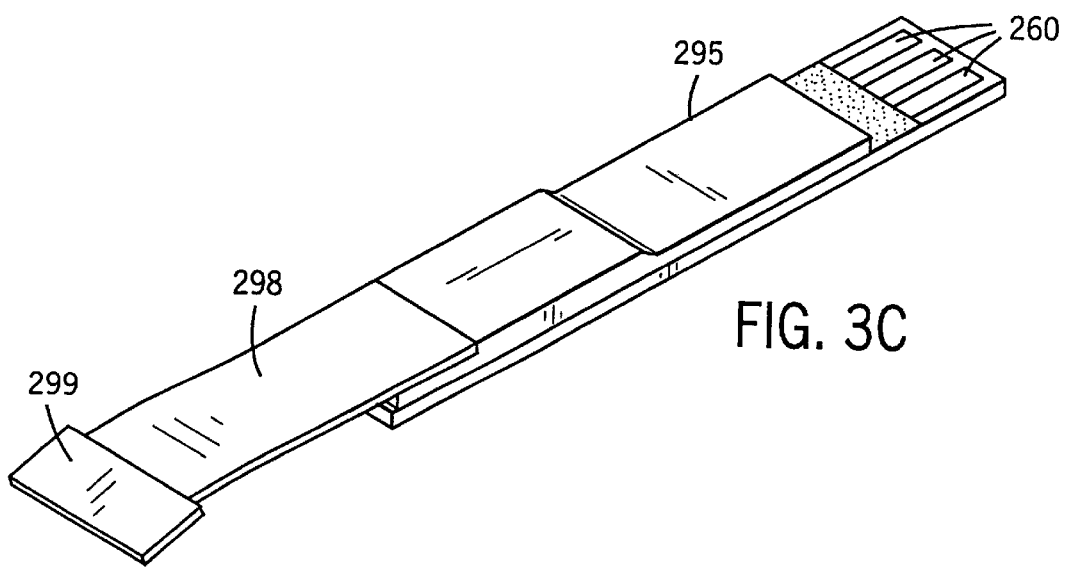
FIG. 3C is a perspective cut-away view of a communications interface in accordance with one embodiment of the invention
Figure 4A:
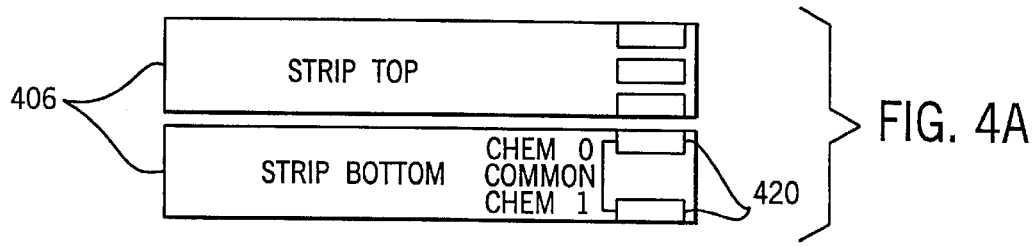
FIG. 4 illustrates examples of various test strips that can be identified using the system of the invention.
Figure 4B:
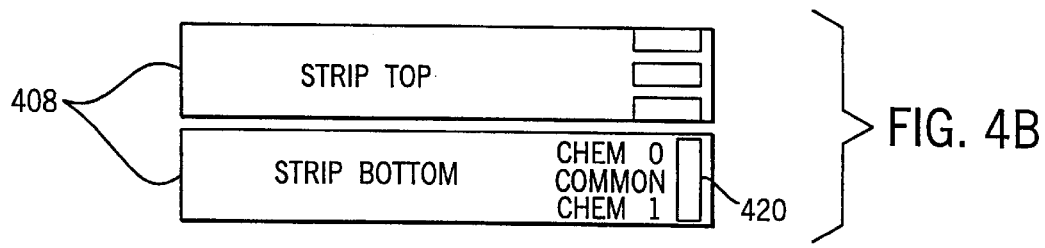
Figure 4C:
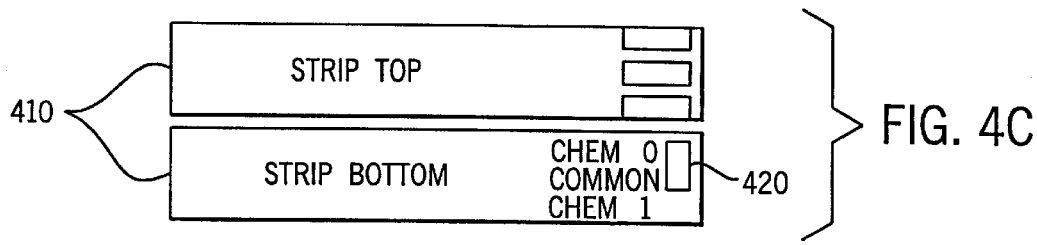
Figure 4D:
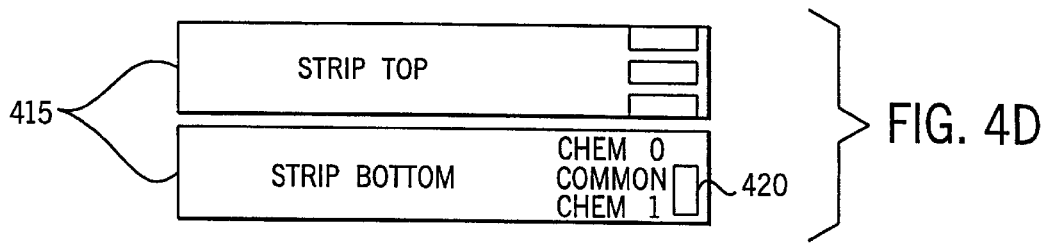

The instrument 100 also features a single multi-purpose test port 110 comprising a slot into which a user inserts test strips (FIG. 3A), calibration strips (FIG. 3B), or a communication interface device (FIG. 3C). These devices and the test port 110 are explained more fully below.

Figure 1B:
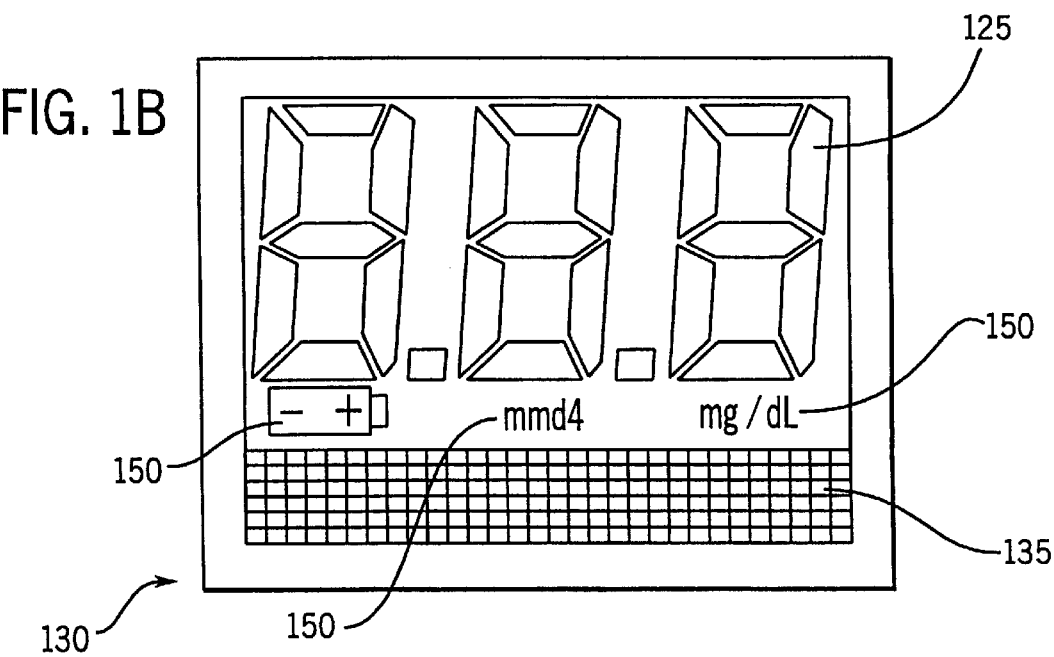
FIG. 1B is an enlarged view of the analyte test instrument display in accordance with an embodiment of the invention.

FIG. 1B shows an embodiment of the display 130 in more detail. The display 130 can be a liquid crystal display (LCD) and is used to display test results, user messages, and recalled information stored on the instrument 100. The results of an assay are displayed in a display 125 that generates three seven-segment numbers. Icons 150 indicate units of measurement (e.g., mg/dL or mmol/L) of the test results and a low battery indication. The display 125, in one embodiment, can display readings with varying levels of precision (e.g., 54.5 mg/dL, 5.45 mg/dL, and the like).

A dot-matrix message line 135 provides information to the user and can generate up to 10 numerals or up to 9 characters. The information displayed can include time and date information, prompts (e.g., "apply blood"), error messages (e.g., "expired strip"), and configuration control (e.g., setting time or selecting a language). Details about these messages, and what causes them to be displayed, are discussed more fully herein.

Display driver software controls the appearance of the display 130 and, in one embodiment, is part of the software 240 of the analyte test instrument (see description of FIG. 2). The display driver software can provide the ability to scroll a long message, alternate two or more strings to display a long message, flash a message or a portion of a message, or display alternating messages. In addition, the display driver software can provide the instrument 100 with the ability to flash the icons 150. Upon power up, the display driver software can support a visual check of the display. That is, the software makes it possible for a user or other entity to perform a visual check of the display. During this process, the icons and the pixels of the dot-matrix display 135 are turned on for a brief period (e.g., a second) to permit the user to check whether the display is functioning properly.

FIG. 2 shows a block diagram of an analyte test system implemented in accordance with one embodiment of the invention. The instrument 100 comprises a processing circuit 210, at least one device circuit 215, a push-button 120, a test port 110, and a display 130. Although not shown, it should be understood that the instrument 100 can further comprise a power supply (e.g., a battery) to provide power to the various electrical components.

The device circuits 215 can comprise analog, digital, or mixed-signal type circuits, application-specific integrated circuits (ASICS), and passive and active electrical components. Device circuits 215 perform various electrical functions required by the analyte test instrument, such as driving the display 130, clock functions for a microprocessor 230, and analog to digital (A/D) conversion of inputs received at the test port 110. It should be understood that functions of the device circuit 215 could be provided by a single electrical component or as part of the processing circuit 210. In one embodiment, the processing circuit 210 comprises a memory 220, a microprocessor 230, and device software 240 in communication with the memory 220 and the microprocessor 230.

In one embodiment, the memory 220 comprises 1K of random access memory (RAM). In some embodiments, the memory 220 has sufficient additional capacity to store a plurality (e.g., four-hundred fifty) of assays. The device software 240 is responsive to information received at the test port 110. The software 240 uses the information to control the operation of the instrument 100. The device software 240 also provides functionality independent of the test port 110. For example, the device software 240 can allow the user to recall assays and assay information, can provide various warning, error, and prompt-type messages, can permit date and time setting, can control transmission of data to external devices, tests, can monitor power and/or battery level, and can provide indications to the user if power becomes too low.

The test port 110 comprises a slot assembly capable of removably receiving a strip device, such as a calibration device 270 (which in some embodiments comprises a calibration strip), a test strip 290, or a communications interface connector strip 295. The test port 110 can have a plurality of contacts capable of electrically engaging such a strip device when inserted into the port. Once a strip is engaged, the test port 110 enables the processing circuit 210 to communicate with the inserted strip. For example, the processing circuit 210 can send signals to test port 110 to determine the identity of the inserted strip. This determination, in some embodiments, can be accomplished using the system described in the co-pending application Ser. No. 09/441,674. In still other embodiments, the identity of the strip may be determined by using resistance measurements. In further embodiments, the identity of the strip may be communicated via an external device. In another embodiment, the communications interface connector 295 is inserted into the test port 110 and transmits signals to facilitate transfer of data from the instrument 100. This feature is also more fully explained below.

In the illustrated embodiment, the test port 110 includes six contacts: CHEM0; CHEM1; NOTOUCH (COMMON); SENS1; SENS 2; and BIASCOM. When a strip is inserted into the test port 110, the bottom major surface and the top major surface of the strip engage the contacts of the test port 110, thereby enabling the instrument to identify a pattern of conductive material on the top major surface and/or the bottom major surface of the strip. In one embodiment, the patterns of conductive material on the inserted strip assist in determination of the type of calibration device 270. In another embodiment, the patterns of conductive material on an inserted strip indicate whether the inserted strip is a calibration device 270, a communications interface connector strip 295, or a test strip 290, and, if a test strip 290, the type of test strip (e.g., glucose, ketone, etc.). The engagement of contacts and the strip identification process are described in more detail in the co-pending application Ser. No. 09/441,674.

FIG. 3A illustrates in more detail the test strip 290. A plurality of contacts 260 is provided at the end of the test strip that is inserted into the test port 110. Typically, a drop of blood is placed for testing on a reaction area 265. When a sufficient quantity of blood is deposited on the reaction area, an electrochemical reaction occurs, causing a flow of electrons that produces an electrical signal, such as a change in current, detectable by the analyte test instrument. The analyte test instrument then converts the detected signal into data corresponding to analyte information and displays the information to the user.

FIG. 3B illustrates a ROM-type calibration strip 270. In one embodiment, a ROM-type calibration strip 270 is associated with a package (not shown) of test strips 290 and contains information specific to that package of test strips 290. The calibration strip 270 has a plurality of contacts 260 at the end that is insertible into test port 110. In one embodiment, the calibration code 275 and manufacturing lot number 285 are printed on the outside of the strip and are visible to the user. In another embodiment, the lot number is stored in the ROM 280 in binary coded decimal (BCD) format.

Parameters and procedures associated with the calibration code 275 and manufacturing lot number 285 are stored on a calibration ROM 280 (hereinafter "the ROM 280"), which is in electrical communication with the contacts 260. For example, the ROM 280 encodes information on the algorithms for performing a strip-based assay and a list of parameters that are essential in characterizing new chemistries, test strips, and marketing requirements. The marketing requirements, in some embodiments, comprise country codes, language information (e.g., pertaining to the language of an insert packaged with the calibration device 270), test strip count (i.e., number of test strips packaged with the calibration device 270), and the like. The calibration device 270 does not itself perform assays. Rather, the calibration strip 270 delivers the necessary parameters and procedures to the instrument to characterize an assay. The ROM 280 has the capability of storing and downloading to the instrument 100 parameters that describe assay phases. Through the sequencing of phases, an assay that compensates for test strip characteristics, new chemistries, and temperature is constructed. The ROM parameters are explained more fully herein.

FIG. 3C illustrates a communications connector strip 295. In one embodiment, the strip is electrically attached through a flexible cable 298 to a connector 299 adapted to mate with a corresponding connector (e.g., DB9 connector) on a data processing device, computer, or other external device (not shown). In one embodiment, the external device contains data communications software that interfaces with the processing circuit 210 and device software 240 for the purpose of receiving and processing analyte data and operational data from the instrument 100. In addition, it should be understood that many different types of computer connectors can be used with the communications connector strip 295 of the present invention.

Referring to FIG. 4, strips 400 (FIG. 4A), 405 (FIG. 4B), 410 (FIG. 4C), and 415 (FIG. 4D) are four different types of test strips. Each type of test strip has a different pattern of conductive material 420 on the bottom major surface of the test strip. In one embodiment, these patterns define different types of glucose test strips. In another embodiment, the patterns define different types of ketone test strips. In still another embodiment, the patterns define ketone, glucose, or other types of test strips.

For each test strip, the conductive material 420 is disposed in such a way that the CHEM0 contact and/or the CHEM1 contact can be tied to a COMMON point (or not be tied at all). Test strip 400 illustrates a test strip in which neither the CHEM0 contact nor the CHEM1 contact is tied to COMMON, which can be used to define a particular type of test strip. Similarly, test strip 410 illustrates the CHEM0 contact being electrically tied to COMMON; test strip 415 illustrates the CHEM1 contact being electrically tied to COMMON; and test strip 405 illustrates both the CHEM1 contact and the CHEM0 contact being electrically tied to COMMON. Each of these test strips can be used to define a particular type of test strip that is different from each other and different from test strip 400. Using a pull-down technique, as is well understood by those skilled in the art, a device circuit 215 such as an ASIC (see FIG. 2) identifies the type of test strip by determining the pattern of connection of the conductive material 420.

Figure 5:
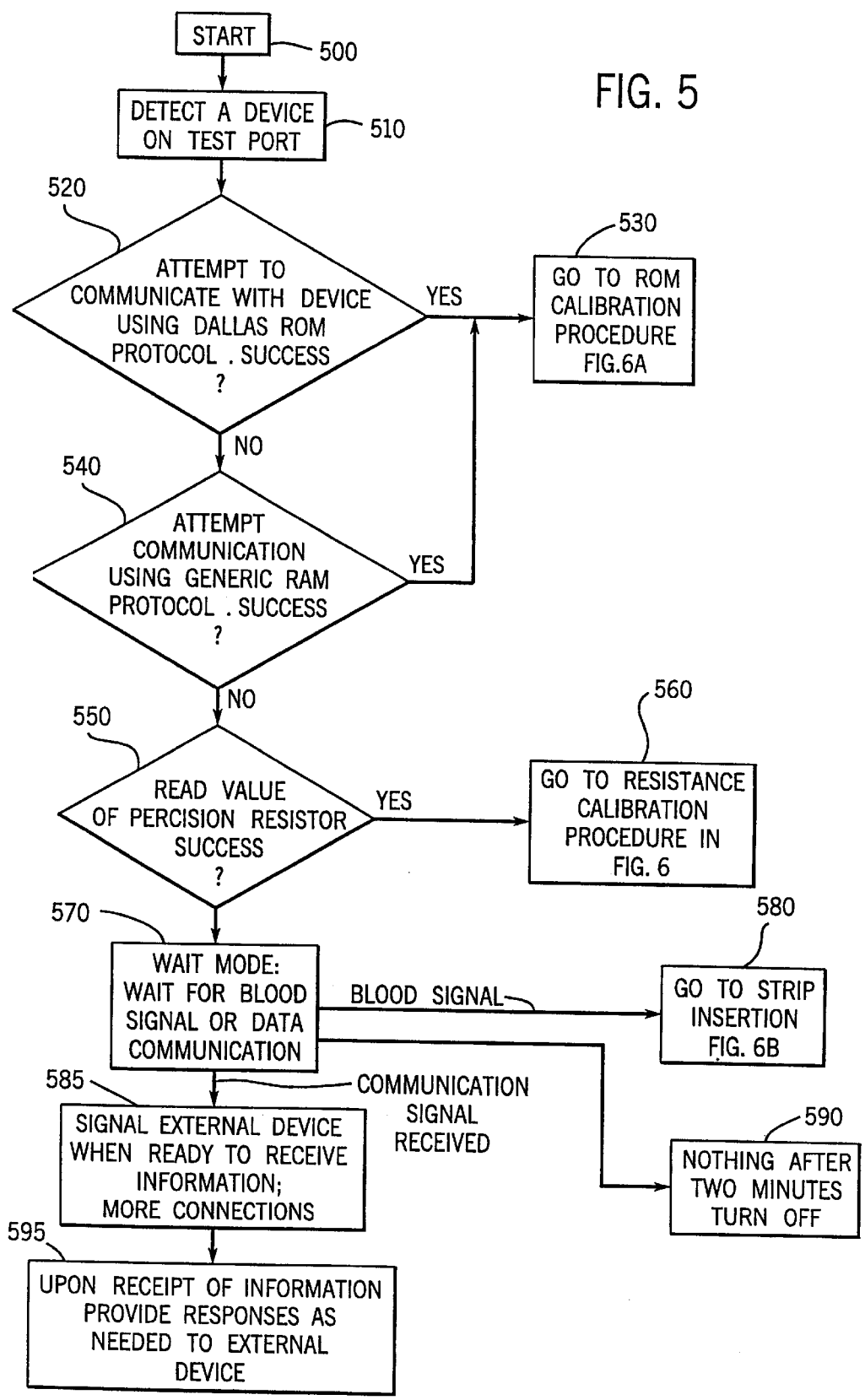
FIG. 5 is a flow chart illustrating a strip identification method in accordance with one embodiment of the invention.

FIG. 5 illustrates a method for identifying a device inserted into the test instrument 100 at test port 110. When a device is inserted into the test port (step 500), the instrument 100 detects it (step 510) and attempts a series of steps (steps 520 through 570) to determine the type of device inserted. First, device software 240 polls the test port 110 to identify the type of device inserted. In one embodiment, the device software 240 attempts to communicate with the device by means of a communications protocol capable of operating with a serial EE-squared interface, such as that defined by the Dallas ROM protocol (step 520) of Dallas Semiconductors, Dallas Tex. As is understood by those skilled in the art, such an interface provides single-wire communication. If successful, the device software 240 proceeds to the ROM calibration procedure illustrated in FIGS. 6A and 6B (step 530). If unsuccessful, the device software 240 attempts to communicate with the device by means of an alternate protocol (for example, the RS-232 standard ROM protocol) (step 540). If successful, the device software 240 proceeds to the ROM calibration procedure of FIG. 6A (step 530).

If device software 240 is unable to communicate with the inserted device by means of predetermined ROM protocols, the software attempts to determine if the device is a resistive calibration device, wherein the device software 240 determines if it can detect and read a precision resistor value (step 550). If successful, the device software 240 proceeds to the resistive calibration procedure. (see step 560 and FIG. 6C, described below).

If the device software 240 is unable to read a precision resistor value, the device software 240 puts the instrument 100 into a brief wait mode (step 570). During the waiting period, the analyte test instrument waits to communicate with an external device or to receive a blood signal. If nothing is received within a predetermined time period, the instrument 100 turns itself off (step 590).

If a blood signal is received, the signal indicates that a user is performing a diagnostic test. Referring briefly to FIG. 3A, as discussed above and in the co-pending application Ser. No. 09/441,674,when a test strip 290 releasably engages the test port 110, the contacts 260 are put in electrical communication with the instrument 100. In one embodiment, when a sample (not shown) is added to the reaction area 265, the sample reacts with an internal test strip circuit (not shown) to put the sample in electrical communication with the contacts 260, and thereby the test port 110. When the instrument 100 detects the presence of the sample, the device software 240 switches the instrument 100 into a test mode and starts the measurement process (step 580).

In one embodiment, during a test of the sample, the instrument 100 analyzes the sample by measuring current through the circuit formed by the sample and the contacts 260. In a further embodiment, the instrument 100 applies current to that circuit to use in subsequent measurements. The use of such a system of test strip electrodes to determine presence and/or concentration of analyte is discussed in U.S. Pat. No. 4,545,382, issued Oct. 8, 1995, and U.S. Pat. No. 4,711,245, issued Dec. 8, 1987, the disclosures of which are incorporated herein by reference. A sensor system that detects current indicative of a compound in a liquid mixture, which system features a test strip adapted for releasable engagement to signal readout circuitry, is discussed in U.S. Pat. No. 5,509,410, the disclosure of which is incorporated herein by reference.

If, when a device is inserted into the test instrument 100, a signal is received, thereby indicating a communication from an external device, such as a personal computer, main-frame computer, or personal digital assistant (PDA), the instrument 100 then signals the external device to indicate that the instrument 100 is ready to receive further information. The instrument 100 also makes the appropriate electrical connections (step 585). Upon receiving information and/or requests for information, the instrument 100 can provide responses as needed to the external device (step 595).

Figure 6A:
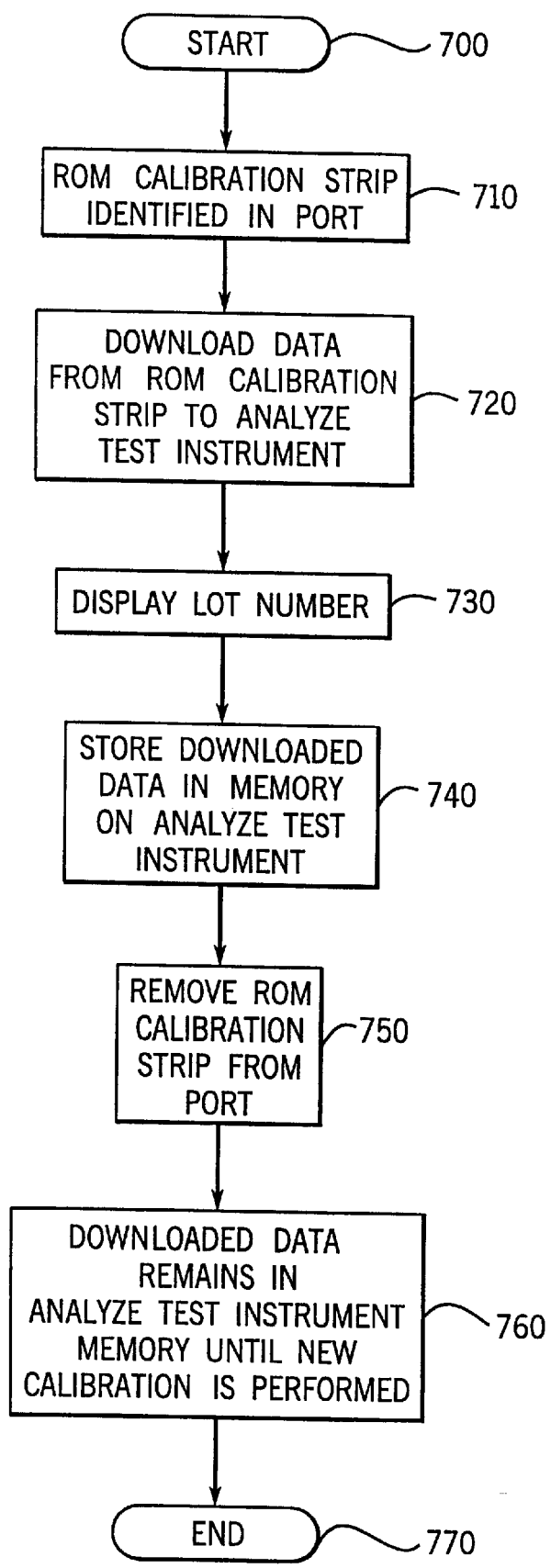
FIG. 6A is a flow chart illustrating a calibration method in accordance with one embodiment of the invention.

FIG. 6A illustrates the ROM calibration procedure for one embodiment of the invention. Upon identifying the calibration strip 270, the device software 240 downloads data from the ROM 280 to the instrument 100 (step 720). In one embodiment, this data is stored in the memory 220. However, the ROM data can be stored anywhere within the instrument 100 so long as the data is accessible even after the calibration device 270 has been removed from the test port 110.

As is explained more fully below, the downloaded data comprises parameters and procedures for controlling the operation of the instrument 100. For example, the data can comprise instrument parameters, test strip parameters, and analyte parameters. The instrument parameters can comprise language and meter type. The test strip parameters can comprise test strip count and expiration date. In addition, the downloaded data can include the lot number of the calibration strip 270.

After the ROM 280 data has been downloaded to the instrument 100, the display 130 displays the lot number downloaded from the calibration device (step 730), as an indication that calibration is complete. Contemporaneously, the instrument 100 stores the downloaded data in the memory (step 740). The user can then remove the calibration strip 270 from the test port 110 (step 750). The downloaded data remains in the memory for use by the instrument 100 until a new calibration procedure is performed (step 760). In some embodiments, the instrument 100 can store more than one set of calibration data in the memory. For example, an instrument 100 capable of performing assays with a plurality of different types of test strips 290 (e.g., glucose, ketones), can store a set of calibration data for each type of test strip 290. In some embodiments, the instrument 100 automatically displays the calibration code associated with a particular type of test strip 290 when the test strip is inserted. Further, the instrument 100 conducts assays using the calibration data associated with the particular type of test strip 290 that is inserted.

The ROM 280 parameters can also comprise marketing parameters, engineering parameters, and assay initialization parameters. Marketing parameters generally are those parameters that vary with the particular package of test strips 290 being used, with the type of calibration device 270 being used, or where (geographically) the instrument is being used. For example, the ROM 280 can provide information to the instrument 100 about the market in which the package of test strips is sold or used. This information can include information about the natural language or group of natural languages that is appropriate with the packaging and inserts for a package of test strips 290.

The strip count is another market parameter that can be provided to the instrument 100 in some embodiments of the invention. The ROM 280 stores the number of test strips 290 included in the box and associated with the calibration strip 270. For example, the calibration strip 270 included with a package of 50 ketone strips could store a strip count of "50", communicating to the instrument 100 that a calibration performed with that calibration strip 270 is effective for, at most, 50 ketone assays. Generally, the strip count associated with a calibration strip 270 for one type of assay (e.g., ketone) is not related to the strip count associated with a calibration strip 270 for another type of assay (e.g., glucose). The strip count is useful for preventing the calibration strip 270 associated with a first package of test strips 290 from being used with another package of test strips, which is likely to have a different calibration code 275 and lot number 285 from that of the first package. In some embodiments, the instrument 110 provides a warning message on the display 130 telling the user that the strip count is exceeded. In other embodiments, the user is prevented ("lock-out") from performing tests on the instrument 110 until the system is calibrated for a new package of test strips. In still other embodiments, both a warning and a lock-out occur when strip count is reached.

Expiration date of the test strips is another parameter provided on the ROM 280. Expiration date is useful to prevent the erroneous results that can occur when testing is done with an expired test strip. When a user inserts the calibration strip 270 to perform calibration, the instrument 100 stores the expiration date provided by ROM 280. If the instrument 100 has not been recalibrated to a later expiration date when the former date is reached, the instrument 100 can provide the user with a warning, a lock-out, or both. In some embodiments, the warning and/or lock-out occurs when a test strip 290 is inserted into the test port 110. In other embodiments, the warning and/or lock-out occurs as soon as the user turns on the instrument 100.

The ROM 280 can also provide an "instrument-type" parameter that corresponds to certain instrument characteristics, functions, and capabilities. This parameter is used to ensure that an incompatible ROM calibration strip is not used to calibrate the instrument.

Another market parameter that can be stored in the ROM 280 is a strip activation parameter, which can enable and disable the calibration capabilities of the instrument 110. In some embodiments, the strip activation parameter includes resistive calibration data to permit calibration of the instrument by means of resistive calibration.

The ROM 280 can also comprise engineering parameters, which control the way the instrument 100 performs tests and, in some cases, what tests the instrument performs. Generally, engineering parameters do not vary by geographic or market location, and are unaffected by expiration date or strip count.

In some embodiments, the engineering parameters comprise a ROM Format ID parameter identifying the ROM 280 to be a particular type and version. For example, the ROM Format ID parameter can identify a ROM 280 as being a "glucose" ROM, meaning that the ROM 280 is storing tests and parameters to perform glucose assays. This embodiment enables the instrument 100 to identify the calibration strip 270 so that a calibration strip 270 that includes a ROM 280 can configure the instrument to perform glucose assays.

In some embodiments, this configuration allows the ROM 280 on the calibration strip to provide parameters and procedures to the instrument 100. In other embodiments, when the instrument 100 identifies the calibration strip 270 to be a glucose strip, the device software 240 runs a glucose procedure itself. In other words, the device software 240 runs a glucose procedure that the instrument 100 already has in the memory, because the procedure has been downloaded from a glucose calibration ROM. In other embodiments, if the ROM Format ID parameter is set to "ketone," the selection of the test to run is. similar to the technique described in connection with the "glucose" tests. In still other embodiments, the ROM format ID can define other types of diagnostic tests or particular testing modes of the instrument.

FIG. 6B is a block diagram showing the overall strip insertion flow process for one embodiment of the invention. In particular, this figure shows a method for operating the instrument to determine whether one or more of the test parameters for the analyte test strips 290 are in error and to display an indication of the invalid strip parameter on the display. During the start period (step 600), the instrument sequences through the steps of FIG. 5 to identify the type of strip. In addition, the device software 240 determines if the expired strip test parameter or the strip count test parameter is invalid. These parameters are described in detail below.

After the instrument 100 has been calibrated according to the procedure shown in FIG. 6A, upon receiving a test strip, the instrument attempts to determine if any of the test parameters stored in the memory are invalid even before the test strip is accepted. For example, if a user attempted to recalibrate the instrument 100 with the same calibration device 270 used previously, but if the calibration device 270 has expired, the user would not be permitted to recalibrate using the calibration device 270. Instead, the instrument 100 displays an error message (step 620) and then shuts itself down (step 680). In another example, if the instrument 100 determines that the test strip count parameter has been exceeded, the instrument displays a warning (step 615) before permitting the user to proceed with testing.

If the instrument 100 finds no strip parameter errors and determines that a glucose test strip or ketone test strip has been inserted, the instrument 100 determines whether the instrument has been calibrated for the type of test strip inserted (step 685). If the instrument has not, a recalibrate message is displayed (step 690) instructing the user to recalibrate the instrument 100.

If, however, the instrument 100 has been calibrated for the type of test strip inserted, the display 130 displays the code corresponding to that of the stored calibration (steps 605 and 610, respectively) before prompting the user to apply blood (step 625). In addition, other information can be presented to the user prior to prompting the user to apply blood, depending on whether the instrument 100 meter was calibrated with a resistive or ROM calibrator. If no blood is detected within five minutes, the instrument is turned off (step 680). In addition, if the test strip is removed before blood is detected, a "no strip" message can be displayed (not shown). After blood is detected (step 626), an "OK" message can be displayed in the text display. Following the test, the result is displayed in the numeric display (step 635 or 650).

Figure 6C:
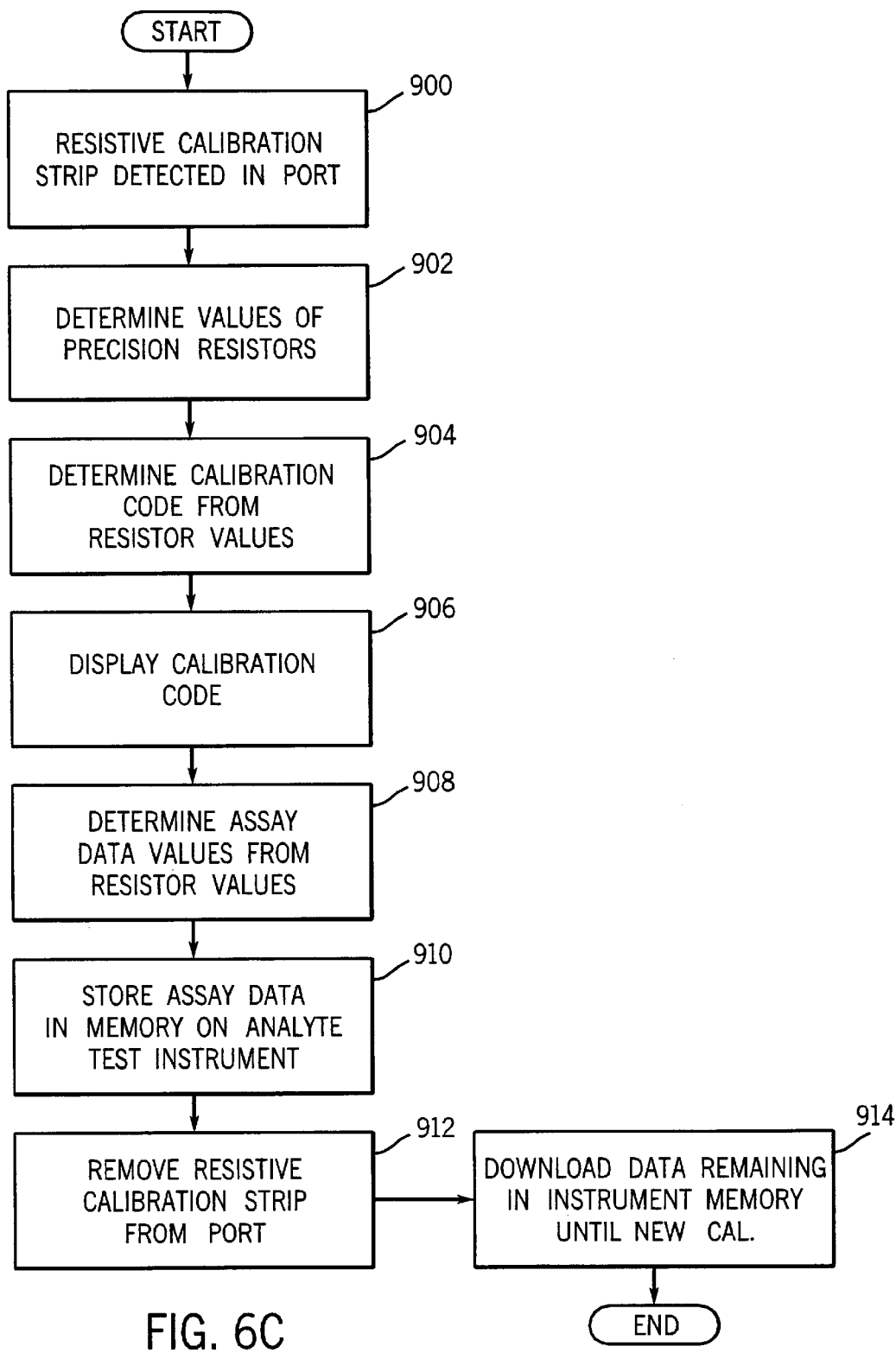
FIG. 6C is a flow chart illustrating a resistive calibration method in accordance with one embodiment of the invention.

FIG. 6C illustrates the resistive calibration procedure, in accordance with one embodiment of the invention. If the device software 240 detects that there is a resistive calibration strip in the port (stop 560 of FIG. 5 and step 900 of FIG. 6C), then the device software 240 determines the values of the precision resistors (902). From the resistor values, a calibration code is determined (step 904). The calibration code is displayed (step 906). Next, the assay data values are determined from the resistor values (step 908).

In one embodiment, assay data values are determined by using the measured resistance value in a table of assay parameters. In another embodiment of the invention, the measured resistance value is used to determine a slope intercept point in one or more graphical representations of assay parameters. In some embodiments, the table or graphical representation of assay parameters is stored in a location on the instrument 100. In still other embodiments, the particular resistance value can also provide an indication of the type of assay in which the resistive calibration strip should be used. The following table illustrates an example of how the measured resistance value is used to provide the assay type and parameters therefor:

TABLE 1

Resistance Values and Assay Type and Parameters

| Resistance value (Ohms) | Assay type | Assay parameters (refers to a set of parameters located in another table, not shown) |
|---|---|---|
| 100–160 | Ketone | Set KA |
| 161–220 | Ketone | Set KB |
| 221–250 | Ketone | Set KC |
| 250–500 | Ketone | Set KD |
| 1K–1.85K | Glucose | Set GA |
| 1.86K–2.35K | Glucose | Set GB |
| 2.36K–2.78K | Glucose | Set GC |
| Over 2.78K | Glucose | Set GD |

It should be understood, however, that the resistance values and assay parameter sets of Table 1 are provided by way of example only. One skilled in the art will recognize that other types of tables, resistance values, and the like, are within the scope of this invention.

After the appropriate assay parameters are obtained, the parameters are stored in the memory on the instrument 100 (step 910). When the resistive calibration strip is removed from the port (step 912), the assay parameters remain in the memory of instrument 100 until a new calibration is performed (step 914).

FIG. 7 illustrates a method for determining the actual date and time of events of a battery-operated test instrument 100 in accordance with one embodiment of the invention. Using this method, the device software 240 of the instrument 100 can determine the correct date and time of a test event when a user has not set the date and time since the last time batteries were properly inserted.

In one embodiment, the device software 240 assumes that the date and time are invalid if date and time have not been set since the last time a power-on-reset (POR) event was detected. (A POR event will not necessarily occur every time the batteries are replaced.) For example, in this embodiment, the device software 240 associates the date and time, and a semaphore "Time Valid", which may be true or false, with each assay result. "Time Valid" semaphore will be true if and only if date and time have been set since the last POR event. In such an embodiment, if the date and time have been set since the last time a POR event was detected, then the date and time have been set properly.

In some embodiments, a POR event can be triggered by insertion or removal of batteries. In other embodiments, a POR event can be triggered by removal of the instrument 100 from a source of power, such as an external power supply, battery pack, or other suitable power source.

When a test event (e.g., an assay) occurs (step 800), the device software 240 first determines whether the date and time have been set properly (step 810). In addition, the device software associates the instrument date and time, along with a "Time Valid" semaphore, with each test event. The "Time Valid" semaphore can be true or false for each assay result. The semaphore is true only if the date and time have been set properly.

If the date and time have not been set properly, the device software 240 assumes that the date and time of the instrument 100 are invalid. Thus, the device software 240 assigns a value to the event, notes that the "Time Valid" semaphore is false, and stores the value of the event and the "Time Valid" semaphore (step 820).

If the date and time have been set properly, then the device software 240 assumes that the date and time of the instrument are valid. Accordingly, it stores the date and time of the event and notes that the "Time Valid" semaphore is true (step 830).

After storing the event, the value (optionally), and the "time-valid" semaphore (step 840), the device software 240 provides a reference date and time to the analyte test instrument (step 850) and assigns a reference value to the reference date and time (step 860). The reference date and time can represent the actual, current date and time. The reference date and time can be provided to the instrument in any one of a number of ways. In one embodiment, the device software 240 establishes communication between an external device and the test instrument 100, then downloads the reference date and time from the external device. In another embodiment, the reference date and time can be entered using the user interface of the instrument 100 (e.g., pushbutton 120). A reference value is then assigned to the reference date and time.

In one embodiment, the test instrument 100 uses the "Time Valid" semaphore, reference date, reference value, and event value to respond to a request for a stored event (e.g., during results recall, averages display, and data uploading). In addition, the instrument offers a "results recall" function that allows a user to view the stored results on the display 130. For each result, if the "Time Valid" semaphore is true (step 880), the date and time associated with the result is shown with the result on the display 130 (step 895).

If the "Time Valid" semaphore is false, the date and time associated with the event must be corrected to reflect the correct date and time. This is done by adjusting the event value using the reference value and reference date and time to achieve the correct date and time (step 890) before providing the event information to the requester (step 895).

If the request for a stored event is for an average over a time period, then the device software 240 filters the stored results, excluding any results for which the "Time Valid" semaphore is false. The time periods for such an average can include a 7-day average, 14-day average, or a 28-day average.

If an external device requests that a stored event be uploaded from the instrument, then the external device adjusts the event value by the reference value to achieve the correct date and time (step 890). In one embodiment, data uploading delivers results, date and time, and a "Time Valid" semaphore for each result uploaded to an external device. In addition, the date and time that the "Time Valid" became false (start of "Time Valid" false period) can be delivered to the external device. In additional embodiments, when the external device has a date and time capability, the date and time of the external device can be used to provide a reference date and time, and reference value, to the instrument 100. In additional embodiments, the external device can automatically provide a reference date and time whenever the instrument 100 is connected to it.

The following example illustrates the operation of this embodiment of the invention. Assume that the events of Table 2 are stored in the memory 220:

been set since the POR event occurred. Note that the date and time are set at a default value when a POR event occurs, namely 01/01/90 00:00. This occurs at each POR event (e.g., in Table 2, after events 4, 9, and 11). As will be explained below, in some embodiments of the invention, the default date and time assist in tracking the date and time of test events that occur even when the "Time Valid" semaphore is false.

In addition, it should be noted that this default date and time is provided by way of example only and other default dates and times can be used. However, in one embodiment, it is preferred that the default date and time be chosen so that the default date and time will not coincide with an actual date and time that could occur. Thus, the instrument software 240 of the example includes a default date and time that are several years previous to the date and time that the instrument is sold 100. In still another example, the default date and time (as well as the date and time) can be in a four-digit year format, e.g., 01/01/1990 00:00, which can be useful to prevent problems that might occur after the year 2000.

Referring again to Table 2, at Event 2, the time and date are set, so the "Time Valid" semaphore becomes "true." At Event 3, a test occurs, i.e., the glucose test shown. At Event 4, the "Time Valid" semaphore remains "true" for the test results, because the POR event did not occur until one hour after the results. Therefore, the date and time of events 6 and 7 (which occur while the "Time Valid" semaphore is "false") occur at times relative to the default POR date and time. When the date and time are set at Event 8, the "Time Valid" semaphore changes to "true," and remains true during Event 9. The POR event after Event 9 again changes the "Time Valid" semaphore to "false". Events 11 through 13 all occur while the "Time Valid" semaphore is "false" (i.e., no resetting of date and time has occurred).

Following the events listed in Table 2, a data upload to an external device is performed. All of the information in Table 2, except the notes and the Event No.'s, is provided in the upload. The upload includes the instrument date of 01/02/90 and time of 02:03 (the time of the upload) and includes information relating to the state of the "Time Valid" sema-

TABLE 2

Date and Time Events

| Event No. | Date | Time | Event (including test measurement) | Time Valid Semaphore | Notes |
|---|---|---|---|---|---|
| 1 | 01/01/90 | 00:00 | POR | false | POR = Power on reset. Date and time at defaults. |
| 2 | 01/01/90 | 01:01 | time change | true | New time = 8/22/98 14:02 |
| 3 | 8/22/98 | 14:03 | glucose 105 | true | |
| 4 | 8/23/98 | 15:04 | ketones 0.4 | true | POR event one hour after result |
| 5 | 01/0190 | 00:00 | POR | false | Date and time at defaults until date and time are set. |
| 6 | 01/02/90 | 6:06 | glucose 125 | false | |
| 7 | 01/03/90 | 07:07 | glucose 201 | false | |
| 8 | 01/04/90 | 08:08 | time change | true | time changed to 8/28/98 18:18 |
| 9 | 8/28/98 | 18:20 | glucose 300 | true | POR 5 minutes after result |
| 10 | 01/01/90 | 00:00 | POR | false | |
| 11 | 01/02/90 | 01:01 | glucose 101 | false | POR 10 minutes after result |
| 12 | 01/01/90 | 00:00 | POR | false | |
| 13 | 01/02/90 | 02:02 | glucose 202 | false | upload performed immediately after result |

At Event 1, the "Time Valid" semaphore is false because a POR event has occurred but the time and date have not phore. The date and time of the external device is 8/31/1998 12:02. The external device assumes that each instance when the user resets the date and time was done properly. Thus, the external device assumes that events labeled with dates 8/22/98, 8/23/98, and 8/28/98 are treated as correct and no further correction is required. Referring to FIG. 8, the events occurring on those dates would correspond to a "true" value (steps 880 and 895), so no correction is required.

The events labeled with dates of 01/02/90 06:06 (Event 6) and 01/03/90 07:07 (Event 7), however, have a "false" value (step 890 of FIG. 8) and require correction. These events can be corrected because the time change event on 08/28/98 indicates a delta time of +8 years, 7 months, 24 days, 10 hours, and 10 minutes. Therefore, the corrected dates and times provided to the external device (step 895) are:

TABLE 3

First Corrected Events

| Date | Time | Event | Time Valid Flag |
|---|---|---|---|
| Aug. 26, 1998 | 16:16 | glucose 125 | back-calculated |
| Aug. 27, 1998 | 17:17 | glucose 201 | back-calculated |

In this embodiment, the date and time of the event labeled 01/01/90 01:01 (Event 11) cannot be determined because the event occurred between two POR events, without a time change between the two POR events. The date and time of the event labeled 01/02/90 02:02 (Event 13) can be determined from the current time in the external device and the time indicated by the device software 240 at the time of the upload. In this example, there is a delta time of +8 years, 7 months, 29 days, 10 hours, and 0 minutes. Therefore, the corrected event is:

TABLE 4

Additional Corrected Event

| Date | Time | Event | Time Valid Flag |
|---|---|---|---|
| Aug. 31, 1998 | 12:02 | glucose 202 | back-calculated |

Any of the embodiments described herein, including all of the functionalities described herein, can be provided as computer software on a computer readable medium such as a diskette or an optical compact disc (CD) for execution on a general purpose computer (e.g., an Apple Macintosh, an IBM PC or compatible, a Sun Workstation, etc.).

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A method for determining the actual date and time of an event measured by an analyte test instrument, said method comprising the steps of:

(a) generating said event by operation of said analyte test instrument;

(b) determining whether said actual date and time of said event have been set properly, when operation of said analyte test instrument has been interrupted on account of removal of said analyte test instrument from a source of power;

(c) if said actual date and time of said event have not been set properly, assigning a time-related value to said event;

(d) storing said event generated by operation of said analyte test instrument in memory;

(e) providing a reference date and time to said analyte test instrument;

(f) assigning a reference value to said reference date and time; and (g) computing said actual date and time of said event by adjusting the time-related value assigned to said event by using said reference value.

2. The method of claim 1, wherein step (c) further comprises the steps of:

(i) establishing communications between an external device and said analyte test instrument; and (ii) downloading said reference date and time from said external device to said analyte test instrument.

3. The method of claim 1, wherein said analyte test instrument comprises a user interface and step (c) further comprises the step of entering said reference date and time into said analyte test instrument using said user interface.

4. The method of claim 1, wherein said analyte test instrument is powered by a battery.

5. The method of claim 4, wherein said step of assigning a value to an event comprises assigning a value to said event when said event is stored in memory and operation of said instrument by said battery has been interrupted.

6. The method of claim 1 further comprising the step of receiving a request from a requester for said stored event.

7. The method of claim 6, further comprising the step of providing to said requester information relating to said stored event.

* * * * *